(12) United States Patent  
Fang et al.

(10) Patent No.: US 8,992,636 B1
(45) Date of Patent: Mar. 31, 2015

(54) ALKOXYLATED QUATERNARY AMMONIUM SALTS AND FUELS CONTAINING THEM

(71) Applicant: Afton Chemical Corporation, Richmond, VA (US)

(72) Inventors: Xinngao Fang, Midlothian, VA (US); Scott D. Schwab, Richmond, VA (US)

(73) Assignee: Afton Chemical Corporation, Richmond, VA (US)

( * ) Notice: Subject to any disclaimer, the term of this patent is extended or adjusted under 35 U.S.C. 154(b) by 0 days.

(21) Appl. No.: 14/048,845

(22) Filed: Oct. 8, 2013

(51) Int. Cl.
| | | |
|---|---|---|
| *C10L 1/22* | (2006.01) | |
| *C10L 1/24* | (2006.01) | |
| *C10L 1/224* | (2006.01) | |
| *C07C 231/14* | (2006.01) | |
| *C07C 237/16* | (2006.01) | |
| *F02B 77/00* | (2006.01) | |

(52) U.S. Cl.
CPC ............... *C10L 1/224* (2013.01); *C07C 231/14* (2013.01); *C07C 237/16* (2013.01); *F02B 77/00* (2013.01)
USPC .............................................. 44/419; 44/405

(58) Field of Classification Search
CPC ..... C10L 1/224; C07C 231/14; C07C 237/16; F02B 77/00
USPC ................ 44/321, 405, 419; 123/1 A; 554/52
See application file for complete search history.

(56) References Cited

U.S. PATENT DOCUMENTS

| | | | |
|---|---|---|---|
| 3,468,816 A * | 9/1969 | Thompson et al. ........... 564/292 |
| 4,482,357 A | 11/1984 | Hanlon | |
| 5,254,138 A * | 10/1993 | Kurek .............................. 44/347 |
| 8,147,569 B2 | 4/2012 | Barton | |
| 2008/0307698 A1* | 12/2008 | Barton et al. .................... 44/321 |
| 2012/0138004 A1* | 6/2012 | Stevenson et al. ............ 123/1 A |
| 2013/0118062 A1* | 5/2013 | Fang et al. ....................... 44/405 |
| 2013/0220255 A1* | 8/2013 | Fang .............................. 123/1 A |

* cited by examiner

*Primary Examiner* — James Goloboy
*Assistant Examiner* — Latosha Hines
(74) *Attorney, Agent, or Firm* — Luedeka Neely Group, P.C.

(57) ABSTRACT

A fuel additive and its preparation for a engine, a fuel containing the additive, a fuel additive concentrate, a method for improving performance of fuel injectors and a method for cleaning fuel injectors for an engine. The fuel additive includes a quaternary ammonium salt derived from a reaction of a hydrocarbyl substituted anhydride, a tertiary amine and a hydroxyl-containing epoxide, wherein the tertiary amine is devoid of primary and secondary amino groups.

15 Claims, No Drawings

ALKOXYLATED QUATERNARY AMMONIUM SALTS AND FUELS CONTAINING THEM

TECHNICAL FIELD

The disclosure is directed to a fuel additive and to fuels that include the additive that are useful for improving the performance of fuel injected engines. In particular the disclosure is directed to an alkoxylated quaternary ammonium salt fuel additive that is effective to enhance the performance of fuel injectors for gasoline and diesel engines.

BACKGROUND AND SUMMARY

It is well known that liquid fuel contains components that can degrade during engine operation and form deposits. Such deposits can lead to incomplete combustion of the fuel resulting in higher emissions and poorer fuel economy. Detergents are well known additives in liquid fuels to help minimize deposit formation. As the dynamics and mechanics of an engine continually advance, the requirements of the fuels and additives must evolve to keep up with these engine advancements. For example, today's engines have injector systems that have smaller tolerances and operate at higher pressure to enhance fuel spray to the compression or combustion chamber. Deposit prevention and reduction has become critical to optimal operation, and therefore there is a need for detergents capable of providing acceptable performance in a liquid fuel to promote optimal engine operation.

Furthermore, there is a dramatic difference between indirect fuel injected diesel engines, and more modern high pressure common rail (HPCR), direct fuel injected diesel engines. Also, low sulfur diesel fuels and ultra low sulfur diesel fuels are now common in the marketplace for such engines. A "low sulfur" diesel fuel means a fuel having a sulfur content of 500 ppm by weight or less based on a total weight of the fuel. An "ultra low sulfur" diesel fuel (ULSD) means a fuel having a sulfur content of 15 ppm by weight or less based on a total weight of the fuel. Fuel injectors in an HPCR engine perform at much higher pressures and temperatures compared to older style engines and fuel injection systems. The combination of low sulfur or ULSD and HPCR engines have resulted in a change to the type of injector deposits and frequency of formation of injector deposits now being found in the marketplace.

Hence, fuel compositions for direct fuel injected engines often produce undesirable deposits in the internal engine surfaces and fuel filters. Accordingly, improved compositions that can prevent deposit build up, maintaining "as new" cleanliness for the vehicle life are desired. Ideally, the same composition that can clean up dirty fuel injectors restoring performance to the previous "as new" condition would be equally desirable and valuable in the attempt to reduce air borne exhaust emissions and to improve the power performance of the engines.

It is known to use certain polyisobutenyl succinimide (PIBSI)-derived quaternary ammonium salt detergents as additives in fuel compositions to promote optimal engine operation, for example, increased fuel economy, better vehicle drivability, reduced emissions and less engine maintenance by reducing, minimizing and controlling deposit formation. Such quaternized detergents are typically derived from traditional PIBSI fuel additive compounds that have pendant tertiary amine sites which can be alkylated, i.e. quaternized, by a quaternizing agent, such as propylene oxide. Examples of such reactions and reaction products are included in U.S. Pat. No. 8,147,569.

A new improved class of quaternary ammonium salt detergents derived from polyisobutenyl succinamides and/or esters have also been disclosed. Such additives are claimed to be more thermally stable than the PIBSI-derived quaternary ammonium salt detergents and may be manufactured by a less energy-intensive process. Examples of such reactions and reaction products are included in U.S. Publication No. 2012/0138004.

Quaternary ammonium salt detergents often require the use of flammable and dangerous epoxides such as propylene oxide and further require the use of specialized and expensive pressure vessels for their production. The alkoxylation step requires a carboxylic acid as proton donor. The resulting carboxylate may lead to deposit formation and other issues related to carboxylate salts being present in the additive and fuel.

In addition, the polyisobutenyl succinamide and/or ester intermediates tend to be very viscous and difficult to handle during the manufacturing process. The reaction products often contain varying amounts of polyisobutenyl succinimides rendering it difficult to charge a correct amount of epoxide and or acid to the reaction mixture.

Lastly, conventional quaternized PIB/amine ammonium salts tend to negatively impact the demulsibility of fuels such as diesel fuels.

The present invention relates to a new class of alkoxylated quaternary ammonium detergents which offer significant improvements over the prior art polyisobutylene succinimide, amide and or ester derived PIB/amine quaternary ammonium salts. The process requires no specialized and/or expensive pressure reactors. The resulting quaternary salts not only afford improved detergency performance but also provide improved demulsibility.

In accordance with the disclosure, exemplary embodiments provide a fuel additive and its preparation for a engine, a fuel containing the additive, a fuel additive concentrate, a method for improving performance of fuel injectors and a method for cleaning fuel injectors for an engine. The fuel additive includes a quaternary ammonium salt derived from a reaction of a hydrocarbyl substituted anhydride, a tertiary amine and a hydroxyl-containing epoxide, wherein the tertiary amine is devoid of primary and secondary amino groups. The fuel additive concentrate comprises the fuel additive and one or more components and/or solvents.

Another embodiment of the disclosure provides a method of improving the injector performance of a direct fuel injected engine. The method includes operating the engine on a fuel composition containing a major amount of fuel and from about 5 to about 200 ppm by weight based on a total weight of the fuel composition of a quaternary ammonium salt derived from a reaction of a hydrocarbyl substituted anhydride, a tertiary amine and a hydroxyl-containing epoxide, wherein the tertiary amine is devoid of primary and secondary amino groups.

A further embodiment of the disclosure provides a method of operating a direct fuel injected diesel engine. The method includes combusting in the engine a fuel composition containing a major amount of fuel and from about 5 to about 200 ppm by weight based on a total weight of the fuel composition of a quaternary ammonium salt from a reaction of a hydrocarbyl substituted anhydride, a tertiary amine and a hydroxyl-containing epoxide, wherein the tertiary amine is devoid of primary and secondary amino groups.

An additional embodiment of the disclosure provides a method for making a quaternary ammonium salt for use as a fuel detergent. The method includes combining, as reactants, a hydrocarbyl substituted anhydride, a tertiary amine and a hydroxyl-containing epoxide, and reacting the reactants under conditions sufficient to form a quaternary ammonium salt. The tertiary amine is devoid of primary and secondary amino groups.

An advantage of the fuel additive described herein is that the additive may not only reduce the amount of deposits forming on fuel injectors and be effective to clean up dirty fuel injectors sufficient to provide improved power recovery to the engine, but the additive may also unexpectedly enhance the demulsibility of the fuel composition.

Additional embodiments and advantages of the disclosure will be set forth in part in the detailed description which follows, and/or can be learned by practice of the disclosure. It is to be understood that both the foregoing general description and the following detailed description are exemplary and explanatory only and are not restrictive of the disclosure, as claimed.

DETAILED DESCRIPTION OF EXEMPLARY EMBODIMENTS

The fuel additive component of the present application may be used in a minor amount in a major amount of fuel and may be added to the fuel directly or added as a component of an additive concentrate to the fuel. A particularly suitable fuel additive component for improving the operation of internal combustion engines may be made by reacting a tertiary amine of the formula

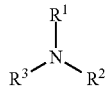

with a hydroxyl-containing epoxide in the presence of an anhydride to provide an alkoxylated quaternary ammonium salt, wherein each of $R^1$, $R^2$, and $R^3$ is selected from hydrocarbyl groups containing from 1 to 200 carbon atoms. The tertiary amine may be reacted with the hydroxyl-containing epoxide and an anhydride to provide the quaternary ammonium salt or the tertiary amine may be an imide-amine that is reacted with a hydroxyl-containing epoxide, provided the imide-amine and tertiary amine are devoid of primary and secondary amino groups. The imide-amine may be derived from a hydrocarbyl-substituted anhydride and an amine having primary and tertiary amino groups and being devoid of secondary amino groups. A key feature of the disclosure is that the quaternary amine reaction product is made in the substantial absence of added acid and/or non-hydroxyl-containing epoxides.

Exemplary tertiary amines include, but are not limited to dimethyl hexylamine, dimethyl octylamine, dimethyl decylamine, dimethyl tetradecylamine, dimethyl pentadecylamine, dimethyl hexadecylamine, dimethyl dodecylamine, dimethyl octadecylamine, diethyl hexylamine, diethyl octylamine, diethyl decylamine, diethyl dodecylamine, diethyl tetradecylamine, diethyl pentadecylamine, diethyl hexadecylamine, diethyl octadecylamine, dipropyl hexylamine, dipropyl octylamine, dipropyl decylamine, dipropyl dodecylamine, dipropyl tetradecylamine, dipropyl pentadecylamine, dipropyl hexadecylamine, dipropyl octadecylamine, oleylamido propyl dimethylamine, $C_9$-$C_{30}$ alkenyl succinimide propyl dimethyl amine, $C_9$-$C_{30}$ alkenyl succinimide propyl dimethyl amine, polyisobutenyl succinimide propyl dimethyl amine, and a poly-tertiary amine. In one embodiment, a tertiary amine including diamines and polyamines may be reacted with a $C_1$ to $C_{54}$ fatty acid to form an amido amine and the amido amine may be subsequently reacted with an anhydride and the hydroxyl-containing epoxide to form the quaternary ammonium salt. Suitable tertiary amido amine compounds of the formula

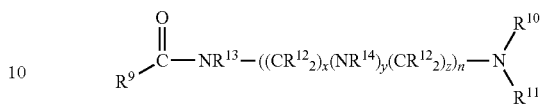

may be used, wherein each of $R^{10}$, $R^{11}$ and $R^{14}$ is selected from hydrocarbyl groups containing from 1 to 50 carbon atoms, each $R^9$, $R^{12}$, and $R^{13}$ may be independently selected from hydrogen or a hydrocarbyl group, x may range from 1 to 6, y may be 0 or 1, z may be 1 to 6, and n may range from 1 to 6. Each hydrocarbyl group $R^9$ to $R^{14}$ may independently be linear, branched, substituted, cyclic, saturated, unsaturated, or contain one or more hetero atoms. Suitable hydrocarbyl groups may include, but are not limited to alkyl groups, aryl groups, alkylaryl groups, arylalkyl groups, alkoxy groups, aryloxy groups, amino groups, and the like. Particularly suitable hydrocarbyl groups may be linear or branched alkyl groups.

As used herein, the term "hydrocarbyl group" or "hydrocarbyl" is used in its ordinary sense, which is well-known to those skilled in the art. Specifically, it refers to a group having a carbon atom directly attached to the remainder of a molecule and having a predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of the description herein, do not alter the predominantly hydrocarbon substituent (e.g., halo (especially chloro and fluoro), hydroxy, alkoxy, mercapto, alkylmercapto, nitro, nitroso, amino, alkylamino, and sulfoxy);

(3) hetero-substituents, that is, substituents which, while having a predominantly hydrocarbon character, in the context of this description, contain other than carbon in a ring or chain otherwise composed of carbon atoms. Hetero-atoms include sulfur, oxygen, nitrogen, and encompass substituents such as pyridyl, furyl, thienyl, and imidazolyl. In general, no more than two, or as a further example, no more than one, non-hydrocarbon substituent will be present for every ten carbon atoms in the hydrocarbyl group; in some embodiments, there will be no non-hydrocarbon substituent in the hydrocarbyl group.

Despite the foregoing definition of a hydrocarbyl group, the $R^1$, $R^2$, and $R^3$ groups of the tertiary amine do not include primary and secondary amino groups.

As used herein, the term "major amount" is understood to mean an amount greater than or equal to 50 wt. %, for example from about 80 to about 98 wt. % relative to the total weight of the composition. Moreover, as used herein, the term "minor amount" is understood to mean an amount less than 50 wt. % relative to the total weight of the composition.

Hydroxyl-Containing Epoxide

A suitable epoxide may be selected from the group consisting compounds of the formula:

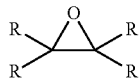

wherein each R is independently selected from H, OH and a $C_1$ to $C_{50}$ hydrocarbyl group, and polyepoxides, provided at least one R includes a primary, secondary or tertiary hydroxyl group. Non-limiting examples of suitable epoxides that may be used as quaternizing agents may be selected from mono- and polyglycidyl ethers of polyalcohols, such as, for example, hydroxymethyl cyclohexene oxide,
butanediol monoglycidyl ether,
propanediol monoglycidyl ether
hexanediol monoglycidyl ether,
cyclohexanedimethanol glycidyl ether,
trimethylolpropane diglycidyl ether,
glycerol diglycidyl ether,
pentaerythritol triglycidyl ether,
glycidol,
3-glycidyloxybenzyl alcohol, and combinations of two or more of the foregoing.

The quaternary ammonium salts from tertiary amines and hydroxyl-containing epoxides may be made in one stage or two stages. The reaction may be carried out by contacting and mixing the hydroxyl-containing epoxide with an anhydride, then contacting and reacting the mixture with the tertiary amine. In another process, all three reactants may be mixed together in a single reaction vessel. In another process, a primary or secondary amine may be first reacted with an electrophile to form a tertiary amine or an imide, amide, or the like devoid of primary and secondary amino groups, and then the tertiary amine is reacted with the hydroxyl-containing epoxide and an anhydride. An important feature of the reaction is that prior to reaction with the epoxide, the tertiary amine is devoid of primary and secondary amino groups. In another important feature of the disclosure is that the reaction is conducted without the addition to the reaction mixture of a carboxylic acid or an acid containing compound.

The reaction may be carried out at temperature ranging from about 30° to about 90° C., for example from about 45° to about 70° C. The reaction may be conducted by reacting any amount of tertiary amino groups to epoxy groups sufficient to provide a quaternary ammonium compound. In one embodiment a mole ratio of tertiary amino groups to epoxy groups may range from about 2:1 to about 1:2. When the reaction is completed volatiles and unreacted reagents may be removed from the reaction product by heating the reaction product under vacuum. The product may be diluted with mineral oil, diesel fuel, kerosene, or an inert hydrocarbon solvent to prevent the product from being too viscous, if necessary.

One or more additional optional compounds may be present in the fuel additive concentrate and/or the fuel compositions of the disclosed embodiments. For example, the fuels may contain conventional quantities of nitrogen-containing detergents, octane improvers cetane improvers, corrosion inhibitors, cold flow improvers (CFPP additive), pour point depressants, solvents, demulsifiers, lubricity additives, friction modifiers, amine stabilizers, combustion improvers, dispersants, antioxidants, heat stabilizers, conductivity improvers, metal deactivators, marker dyes, organic nitrate ignition accelerators, cyclomatic manganese tricarbonyl compounds, and the like. In some aspects, the compositions described herein may contain about 60 weight percent or less, or in other aspects, about 50 weight percent or less, based on the total weight of the additive concentrate, of one or more of the above additives. Similarly, the fuels may contain suitable amounts of conventional fuel blending components such as methanol, ethanol, butanol, isobutanol, fatty acid alkyl ester, dialkyl ethers, 2-ethylhexanol, and the like.

In some aspects of the disclosed embodiments, organic nitrate ignition accelerators that include aliphatic or cycloaliphatic nitrates in which the aliphatic or cycloaliphatic group is saturated, and that contain up to about 12 carbons may be used. Examples of organic nitrate ignition accelerators that may be used are methyl nitrate, ethyl nitrate, propyl nitrate, isopropyl nitrate, allyl nitrate, butyl nitrate, isobutyl nitrate, sec-butyl nitrate, tert-butyl nitrate, amyl nitrate, isoamyl nitrate, 2-amyl nitrate, 3-amyl nitrate, hexyl nitrate, heptyl nitrate, 2-heptyl nitrate, octyl nitrate, isooctyl nitrate, 2-ethylhexyl nitrate, nonyl nitrate, decyl nitrate, undecyl nitrate, dodecyl nitrate, cyclopentyl nitrate, cyclohexyl nitrate, methylcyclohexyl nitrate, cyclododecyl nitrate, 2-ethoxyethyl nitrate, 2-(2-ethoxyethoxy)ethyl nitrate, tetrahydrofuranyl nitrate, and the like. Mixtures of such materials may also be used.

Examples of suitable optional metal deactivators useful in the compositions of the present application are disclosed in U.S. Pat. No. 4,482,357 issued Nov. 13, 1984, the disclosure of which is herein incorporated by reference in its entirety. Such metal deactivators include, for example, salicylidene-o-aminophenol, disalicylidene ethylenediamine, disalicylidene propylenediamine, and N,N'-disalicylidene-1,2-diaminopropane.

When formulating the fuel compositions of this application, the additives may be employed in amounts sufficient to reduce or inhibit deposit formation in a fuel system or combustion chamber of an engine and/or crankcase. In some aspects, the fuels may contain minor amounts of the above described reaction product that controls or reduces the formation of engine deposits, for example injector deposits in diesel engines. For example, the fuels of this disclosure may contain, on an active ingredient basis, an amount of the quaternary ammonium salt in the range of about 1 mg to about 200 mg of quaternary ammonium salt per Kg of fuel, such as in the range of about 5 mg to about 50 mg of per Kg of fuel or in the range of from about 5 mg to about 25 mg of the quaternary ammonium salt per Kg of fuel. The active ingredient basis excludes the weight of (i) unreacted components associated with and remaining in the product as produced and used, and (ii) solvent(s), if any, used in the manufacture of the product either during or after its formation.

The additives of the present application, including the quaternary ammonium salt described above, and optional additives used in formulating the fuels of this invention may be blended into the base fuel individually or in various subcombinations. In some embodiments, the additive components of the present application may be blended into the fuel concurrently using an additive concentrate, as this takes advantage of the mutual compatibility and convenience afforded by the combination of ingredients when in the form of an additive concentrate. Also, use of a concentrate may reduce blending time and lessen the possibility of blending errors.

The fuels of the present application may be applicable to the operation of gasoline and diesel engines. The engine include both stationary engines (e.g., engines used in electrical power generation installations, in pumping stations, etc.) and ambulatory engines (e.g., engines used as prime movers in automobiles, trucks, road-grading equipment, military vehicles, etc.). For example, the fuels may include any and all gasoline grades, middle distillate fuels, diesel fuels, biorenewable fuels, biodiesel fuel, fatty acid alkyl ester, gas-to-liquid (GTL) fuels, jet fuel, alcohols, ethers, kerosene, low sulfur fuels, synthetic fuels, such as Fischer-Tropsch fuels, liquid petroleum gas, bunker oils, coal to liquid (CTL) fuels, biomass to liquid (BTL) fuels, high asphaltene fuels, fuels derived from coal (natural, cleaned, and petcoke), genetically engineered biofuels and crops and extracts therefrom, and natural gas. "Biorenewable fuels" as used herein is understood to mean any fuel which is derived from resources other than petroleum. Such resources include, but are not limited to, corn, maize, soybeans and other crops; grasses, such as switchgrass, miscanthus, and hybrid grasses; algae, seaweed, vegetable oils; natural fats; and mixtures thereof. In an aspect, the biorenewable fuel can comprise monohydroxy alcohols, such as those comprising from 1 to about 5 carbon atoms. Non-limiting examples of suitable monohydroxy alcohols include methanol, ethanol, propanol, n-butanol, isobutanol, t-butyl alcohol, amyl alcohol, and isoamyl alcohol.

Accordingly, aspects of the present application are directed to methods for reducing the amount of injector deposits of engines having at least one combustion chamber and one or more direct fuel injectors in fluid connection with the combustion chamber. In another aspect, the quaternary ammonium salts described herein or fuel containing the quaternary ammonium salt may be combined with polyhydrocarbyl-succinimides, -acids, -amides, -esters, -amide/acids, -acid/esters, -Mannich compounds, polyhydrocarbyl amines, and polyether amines.

In some aspects, the methods comprise injecting a hydrocarbon-based fuel comprising a quaternary ammonium salt of the present disclosure through the injectors of the engine into the combustion chamber, and igniting the fuel. In some aspects, the method may also comprise mixing into the fuel at least one of the optional additional ingredients described above.

EXAMPLES

The following examples are illustrative of exemplary embodiments of the disclosure. In these examples as well as elsewhere in this application, all parts and percentages are by weight unless otherwise indicated. It is intended that these examples are being presented for the purpose of illustration only and are not intended to limit the scope of the invention disclosed herein.

Comparative Example 1

A quaternary ammonium salt was prepared by a method according to U.S. Pat. No. 8,147,569. To a mixture of PIBSI (reaction product of polyisobutenyl succinic anhydride (PIBSA) and dimethylaminopropyl amine (DMAPA), 1:1) (249 grams) made according to U.S. Pat. No. 8,147,569 and aromatic solvent aromatic (70 grams) was added acetic acid (17.3 grams), 1,2-butylene oxide (34.6 grams), isopropanol (64 grams), and 2-ethylhexanol (18 grams). The mixture was heated at 50° C. for 1 hour, then at 55° C. for 2 hours and 15 minutes, 60° C. for 2 hours, and 65° C. for 5 hours. Volatiles were removed under reduced pressure at 65° C. to give product as a brown viscous oil containing the quaternary ammonium salt.

Comparative Example 2

A quaternary ammonium salt was prepared by a method according U.S. Publication No. 2012/0138004. According to the procedure of "preparatory material A", a mixture of PIBSA (PIB Mn=950, 225 grams) and aromatic solvent (91 grams) was heated to 45° C. DMAPA (23.4 grams) was added over 10 minutes to keep the mixture temperature from rising above 60° C. It was found the reaction mixture was very viscous and was difficult to stir. The mixture was stirred at 60° C. for 2 hours. Then 2-ethyl hexanol (68 grams) and 1,2-butylene oxide (33.4 grams) were added to the reaction product. The resulting mixture was heated at 55° C. for 1 hour, 60° C. for 1 hour, 62.5° C. for 2 hours, and 65° C. for 1 hour. Volatiles were removed under reduced pressure to give the quaternary ammonium salt product as a brownish oil.

Inventive Example 1

A mixture of PIBSA (229 grams) and glycidol (17.4 grams) and aromatic solvent (53 grams) was heated to 45° C. for 30 minutes. Oleylamido propyl dimethylamine (86 grams) was added to the mixture slowly to keep the temperature below 52° C. Then 2-ethylhexanol (94 grams) was added to the mixture. The final mixture was reacted at 55° C. for 1 hour, then 60° C. for 2.5 hours, and 65° C. for 1 hour to give product as a viscous oil.

Inventive Example 2

A quaternary ammonium salt was prepared similarly to that of Inventive Example 1 except that a $C_{20}$-$C_{24}$ alkenyl succinic anhydride was used in place of PIBSA.

Inventive Example 3

A quaternary ammonium salt was prepared similarly to that of Inventive Example 1 except that dodecyldimethylamine was used in place of oleylamido propyl dimethylamine.

Inventive Example 4

A quaternary ammonium salt was prepared similarly to that of Inventive Example 1 except that the tertiary amine used for the reaction was the reaction product of dodecyl succinic anhydride (DDSA) and dimethylaminopropylamine (DMAPA), and the reaction product of DDSA and DMAPA was used in place of oleylamido propyl dimethylamine.

Inventive Example 5

An aromatic solvent (86 grams) and PIBSI (263 grams) made according to Comparative Example 1 was added to acetic anhydride (26.5 grams). The mixture was heated at 36° C. and glycidol (19 grams) was added in less than 1 minute. The temperature of the mixture rose to 55° C. The mixture was then stirred at 50° C. for 30 minutes. To the mixture was added 2-ethylhexanol (49 grams). The resulting mixture was reacted at 55° C. for 1 hour, 60° C. for 1 hour, 65° C. for 6.5 hours to give product as a brownish oil.

In the following example, an injector deposit test was performed on a diesel engine using an industry standard diesel engine fuel injector test, CEC F-98-08 (DW10) as described below. Table 2 contains the results of the DW10 test conducted on a soy methyl ester B10 diesel fuel and Table 3 contains the results of the DW10 test conducted on a reference PC10 fuel.

Diesel Engine Test Protocol

A DW10 test that was developed by Coordinating European Council (CEC) was used to demonstrate the propensity of fuels to provoke fuel injector fouling and was also used to demonstrate the ability of certain fuel additives to prevent or control these deposits. Additive evaluations used the protocol of CEC F-98-08 for direct injection, common rail diesel engine nozzle coking tests. An engine dynamometer test stand was used for the installation of the Peugeot DW10 diesel engine for running the injector coking tests. The engine was a 2.0 liter engine having four cylinders. Each combustion chamber had four valves and the fuel injectors were DI piezo injectors have a Euro V classification.

The core protocol procedure consisted of running the engine through a cycle for 8-hours and allowing the engine to soak (engine off) for a prescribed amount of time. The foregoing sequence was repeated four times. At the end of each hour, a power measurement was taken of the engine while the engine was operating at rated conditions. The injector fouling propensity of the fuel was characterized by a difference in observed rated power between the beginning and the end of the test cycle.

Test preparation involved flushing the previous test's fuel from the engine prior to removing the injectors. The test injectors were inspected, cleaned, and reinstalled in the engine. If new injectors were selected, the new injectors were put through a 16-hour break-in cycle. Next, the engine was started using the desired test cycle program. Once the engine was warmed up, power was measured at 4000 RPM and full load to check for full power restoration after cleaning the injectors. If the power measurements were within specification, the test cycle was initiated. The following Table 1 provides a representation of the DW10 coking cycle that was used to evaluate the fuel additives according to the disclosure.

TABLE 1

One hour representation of DW10 coking cycle.

| Duration (minutes) | Engine speed (rpm) | Load (%) | Torque (Nm) | Boost air after Intercooler (° C.) |
|---|---|---|---|---|
| 2 | 1750 | 20 | 62 | 45 |
| 7 | 3000 | 60 | 173 | 50 |
| 2 | 1750 | 20 | 62 | 45 |
| 7 | 3500 | 80 | 212 | 50 |
| 2 | 1750 | 20 | 62 | 45 |
| 10 | 4000 | 100 | * | 50 |
| 2 | 1250 | 10 | 25 | 43 |
| 7 | 3000 | 100 | * | 50 |
| 2 | 1250 | 10 | 25 | 43 |
| 10 | 2000 | 100 | * | 50 |
| 2 | 1250 | 10 | 25 | 43 |
| 7 | 4000 | 100 | * | 50 |

Various fuel additives were tested using the foregoing engine test procedure in an ultra low sulfur diesel fuel containing zinc neodecanoate, 2-ethylhexyl nitrate, and a fatty acid ester friction modifier (base fuel). A "dirty-up" phase consisting of base fuel only with no additive was initiated, followed by a "clean-up" phase consisting of base fuel with additive. All runs were made with 8 hour dirty-up and 8 hour clean-up unless indicated otherwise. The percent power recovery was calculated using the power measurement at end of the "dirty-up" phase and the power measurement at end of the "clean-up" phase. The percent power recovery was determined by the following formula Percent Power recovery=(DU−CU)/DU×100 wherein DU is a percent power loss at the end of a dirty-up phase without the additive, CU is the percent power at the end of a clean-up phase with the fuel additive, and power is measured according to CEC F98-08 DW10 test.

TABLE 2

| Additives and treat rate (ppm by weight) | Power loss % DU | CU | Power recovery % (DU-CU)/ DU × 100 | Additive Efficiency Power Recovery %/ppm |
|---|---|---|---|---|
| Comparative Example 1 (100 ppm) | −5.87 | −2.93 | 50 | 0.50 |
| Inventive Example 1 (100 ppm) | −4.99 | −1.29 | 74 | 0.74 |
| Inventive Example 2 (50 ppm) | −4.77 | −1.39 | 71 | 1.42 |

TABLE 3

| Additives and treat rate (ppm by weight) | Power loss % DU | CU | Power recovery % (DU-CU)/ DU × 100 | Additive Efficiency Power Recovery %/ppm |
|---|---|---|---|---|
| Comparative Example 2 (75 ppm) | −5.75 | −0.09 | 98 | 1.30 |
| Inventive Example 1 (75 ppm) | −5.17 | −0.47 | 91 | 1.21 |
| Inventive Example 2 (75 ppm) | 5.53 | 0.99 | 118 | 1.57 |

In Tables 2 and 3, the "Additive Efficiency" is the percent recovery for each part per million of additive in the fuel.

A demulsibility test according to ASTM D-1094 was conducted on several samples in order to determine the impact on fuel demulsibility of the reaction products in a fuel. The fuel used for the test was an ultra low sulfur diesel (ULSD) fuel having a pH buffered at 7 and including the additive at a treat rate of 200 ppm. The fuel also contained 10 ppm commercial polyglycol demulsifier. The results are shown in the following table.

TABLE 4

| Base ULSD fuel + Additive | Full Water Recovery Time | 1b Time | Interface rating at 5 minutes | Separation at 5 minutes | Fuel clarity at 5 minutes |
|---|---|---|---|---|---|
| No additive | 55 seconds | 1 minute | 1 | 1 | 1 |
| Comparative Ex. 1 | Not achieved | Not achieved | 2 | 1 | 1 |
| Comparative Ex. 2 | Not achieved | Not a chieved | 2 | 1 | 1 |
| Inventive Ex. 1 | 3 min. 15 sec. | 4 min. 25 sec. | 1b | 1 | 1 |
| Inventive Ex. 2 | 4 min. 50 sed. | 5 min. | 1b | 1 | 1 |

It was surprisingly found that Inventive Examples 1 and 2 made with a hydroxyl substituted epoxide had superior demulsifibility compared to Comparative Example 1 when tested according to ASTM D-1094. Accordingly, Inventive Examples 1 and 2 not only exhibit surprisingly superior injector cleaning attributes as shown by the power recovery in Tables 2 and 3, but also superior demulsibility compared to Comparative Examples 1 and 2 made by the comparative processes.

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A fuel additive for a fuel injected engine comprising a quaternary ammonium salt derived from a reaction of a hydrocarbyl substituted anhydride, a tertiary amine and a hydroxyl-containing epoxide selected from the group consisting of hydroxymethyl cyclohexene oxide, butanediol monoglycidyl ether, propanediol monoglycidyl ether, hexanediol monoglycidyl ether, cyclohexanedimethanol glycidyl ether, trimethylolpropane diglycidyl ether, glycerol diglycidyl ether, pentaerythritol triglycidyl ether, glycidol, 3-glycidyloxybenzyl alcohol, and combinations of two or more of the foregoing, wherein the tertiary amine is devoid of primary and secondary amino groups.

2. The fuel additive of claim 1, wherein the reaction is conducted without the addition of a carboxylic acid or an acid containing compound to the reactants.

3. The fuel additive of claim 1, wherein the hydrocarbyl group of the hydrocarbyl substituted anhydride is selected from $C_9$-$C_{30}$ alkenyl groups and polyisobutenyl groups.

4. The fuel additive of claim 1, wherein the amine is selected from the group consisting of oleylamido propyl dimethylamine, and dodecyldimethylamine.

5. The fuel additive of claim 1, wherein the tertiary amine comprises compounds of the formula

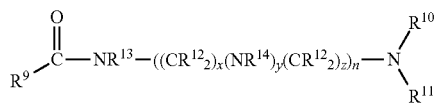

wherein each of $R^{10}$, $R^{11}$ and $R^{14}$ is selected from hydrocarbyl groups containing from 1 to 50 carbon atoms, $R^9$ is selected from hydrogen or a hydrocarbyl group, $R^{12}$, and $R^{13}$ may be independently selected from a hydrocarbyl group, x may range from 1 to 6, y may be 0 or 1, z may be 1 to 6, and n may range from 1 to 6.

6. A fuel composition comprising from about 5 to about 200 ppm of the fuel additive of claim 1 based on a total weight of the fuel composition.

7. A diesel fuel composition comprising from about 10 to about 200 ppm of the fuel additive of claim 1 based on a total weight of the fuel composition, wherein the fuel composition exhibits injector cleaning attributes and full water recovery and an interface rating of 1b in a demulsibility test according to ASTM D-1094.

8. A method of improving the injector performance of a direct fuel injected engine comprising operating the engine on a fuel composition comprising a major amount of fuel and from about 5 to about 200 ppm by weight based on a total weight of the fuel composition of a quaternary ammonium salt derived from a reaction of a hydrocarbyl substituted anhydride, a tertiary amine and a hydroxyl-containing epoxide selected from the group consisting of hydroxymethyl cyclohexene oxide, butanediol monoglycidyl ether, propanediol monoglycidyl ether, hexanediol monoglycidyl ether, cyclohexanedimethanol glycidyl ether, trimethylolpropane diglycidyl ether, glycerol diglycidyl ether, pentaerythritol triglycidyl ether, glycidol, 3-glycidyloxybenzyl alcohol, and combinations of two or more of the foregoing, wherein the tertiary amine is devoid of primary and secondary amino groups.

9. The method of claim 8, wherein the engine comprises a direct fuel injected diesel engine.

10. The method of claim 8, wherein the engine comprises a direct fuel injected gasoline engine.

11. The method of claim 8, wherein the tertiary amine comprises an amido amine derived from an acid compound having from about 1 to about 54 carbon atoms.

12. The method of claim 8, wherein the fuel composition contains from about 10 to about 50 ppm of the quaternary ammonium salt based on a total weight of the fuel composition.

13. A method of operating a direct fuel injected diesel engine comprising combusting in the engine a fuel composition comprising a major amount of fuel and from about 5 to about 200 ppm by weight based on a total weight of the fuel composition of a quaternary ammonium salt derived from a reaction of a hydrocarbyl substituted anhydride, a tertiary amine and a hydroxyl-containing epoxide selected from the group consisting of hydroxymethyl cyclohexene oxide, butanediol monoglycidyl ether, propanediol monoglycidyl ether, hexanediol monoglycidyl ether, cyclohexanedimethanol glycidyl ether, trimethylolpropane diglycidyl ether, glycerol diglycidyl ether, pentaerythritol triglycidyl ether, glycidol, 3-glycidyloxybenzyl alcohol, and combinations of two or more of the foregoing, wherein the tertiary amine is devoid of primary and secondary amino groups.

14. A method for making a quaternary ammonium salt for use as a fuel detergent comprising
combining, as reactants, a hydrocarbyl substituted anhydride, a tertiary amine and a hydroxyl-containing epoxide selected from the group consisting of hydroxymethyl cyclohexene oxide, butanediol monoglycidyl ether, propanediol monoglycidyl ether, hexanediol monoglycidyl ether, cyclohexanedimethanol glycidyl ether, trimethylolpropane diglycidyl ether, glycerol diglycidyl ether, pentaerythritol triglycidyl ether, glycidol, 3-glycidyloxybenzyl alcohol, and combinations of two or more of the foregoing, and
reacting the reactants under conditions sufficient to form a quaternary ammonium salt, wherein the tertiary amine is devoid of primary and secondary amino groups.

15. The method of claim 14, wherein the combining and reaction steps are conducted without the addition of a carboxylic acid or an acid containing compound to the reactants.

* * * * *